United States Patent [19]

Rowlands et al.

[11] Patent Number: 5,339,693
[45] Date of Patent: Aug. 23, 1994

[54] APPARATUS AND METHOD FOR TESTING TUBULAR PRODUCTS

[75] Inventors: Robert E. Rowlands, Madison, Wis.; Edmond P. Saliklis, Lemont, Ill.; John T. Wise, Hartsville, S.C.; Terry D. Gerhardt, Madison, Wis.

[73] Assignee: Sonoco Products Company, Hartsville, S.C.

[21] Appl. No.: 997,232

[22] Filed: Dec. 28, 1992

[51] Int. Cl.⁵ .................................................. G01N 3/10
[52] U.S. Cl. ..................................... 73/825; 73/49.5; 73/821
[58] Field of Search ............... 73/818, 820, 821, 825, 73/37, 49.5, 49.6

[56] References Cited

U.S. PATENT DOCUMENTS 2,268,262 12/1941 Miller .
2,950,620 8/1960 Magill .
3,025,208 3/1962 Geiger .
3,249,964 5/1966 Shaler .
3,856,608 12/1974 Menzies et al. .
3,906,782 9/1975 Early et al. .
3,992,928 11/1976 Thoms .
4,192,194 3/1980 Holt .
4,361,085 11/1982 Schutz .

FOREIGN PATENT DOCUMENTS 3110935 10/1982 Fed. Rep. of Germany .
257823 8/1988 U.S.S.R. ..................................... 73/825

Primary Examiner—Robert Raevis
Attorney, Agent, or Firm—Bell, Seltzer, Park & Gibson

[57] ABSTRACT

Apparatus and method for experimentally determining the compressive material strength of tubular products includes a housing having a cylindrical cavity therein, top and bottom end caps closing opposite ends of the cavity, tubular bladder means mounted in the cavity and defining a pressure chamber larger than the tubular products to be tested and a fluid receiving space between the bladder means and the wall of the cavity, a plurality of small balls substantially filling the pressure chamber around the tubular product being tested, means for pumping hydraulic fluid into the fluid receiving space to cause the bladder means to apply pressure uniformly to said small balls and thence uniformly over the external curved surface of the tubular product. Means are included to continuously monitor and display the magnitude of the pressure applied to the tubular specimen, and to detect and signal tube failure. Tubular specimens can be instrumented to monitor additional testing characteristics. The tubes can be inserted into or removed from the apparatus, as can the balls, without disrupting the hydraulic seal. Tubes of varying dimensions, geometry and material can be tested in the same fixture.

17 Claims, 3 Drawing Sheets

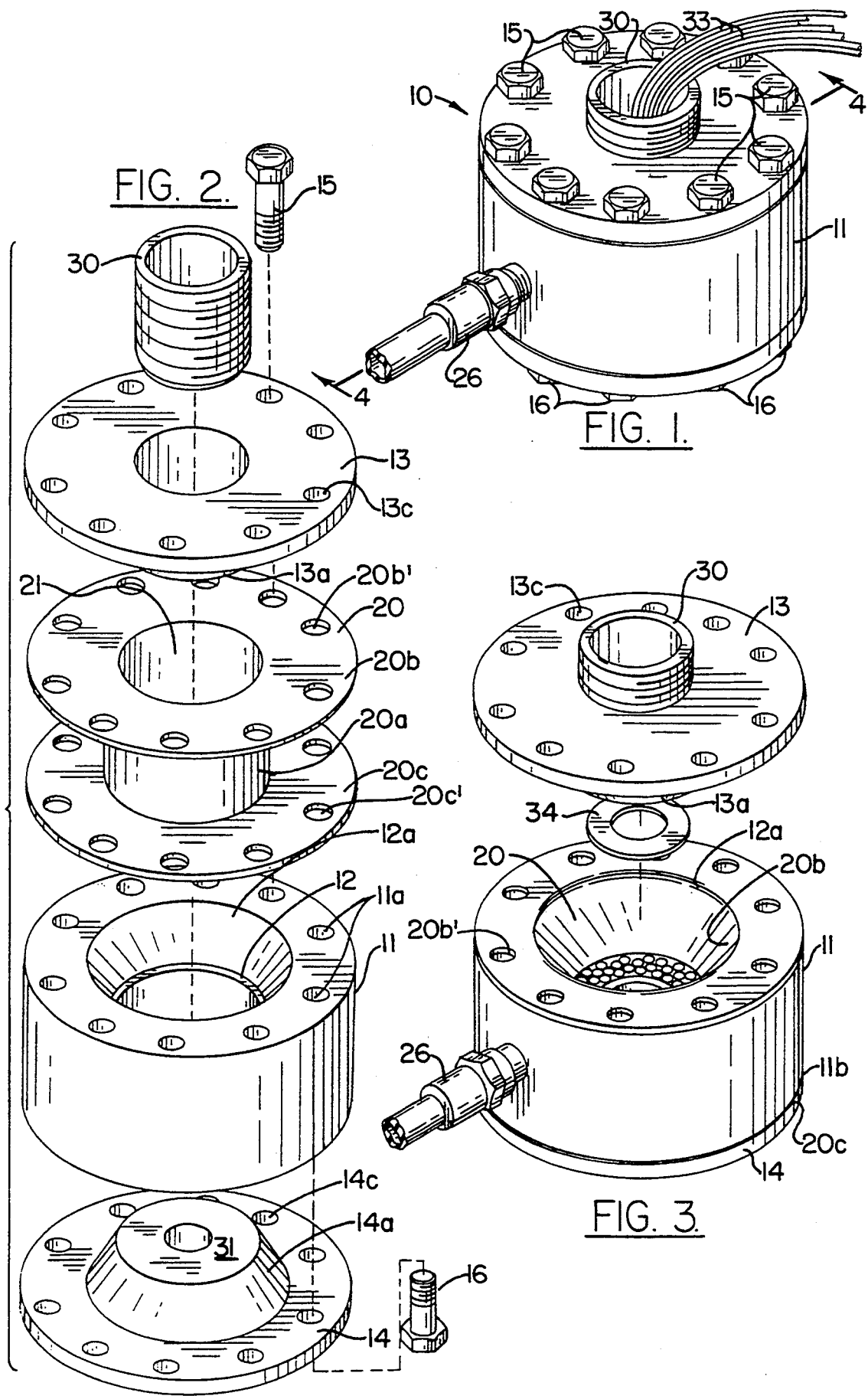

APPARATUS AND METHOD FOR TESTING TUBULAR PRODUCTS

FIELD OF THE INVENTION

This invention relates to the testing of tubular products and more particularly to the testing of such products to determine the compressive strength thereof.

BACKGROND OF THE INVNETION

Cylindrical cores and tubular containers are very widely used for various and sundry purposes. In use, the cylindrical cores and many of the tubular containers (hereinafter referred to as "tubular products" or just "tubes") are subjected to compressive hoop stress due to radial compression or pressure on their outside curved surface. A tubular product's ability to withstand such service conditions and thereby perform its purpose and satisfy end-users' needs without operational difficulties necessitates that it possess sufficient compressive strength. Manufacturers of such tubular products must have quality assurance capabilities to ensure that their tubular products have the requisite compressive strength characteristics.

One of the principal requirements of an effective quality assurance program is a quality-control test to measure reliably the compressive material strength of production tubular products. While several different methods of testing tubular products are currently in use, such currently available testing methods do not address the needs of either the manufacturer or the consumer. For example, a diametral compression flat crush test method is currently in use. While such a test can be useful for comparative purposes, it neither measures the material's compressive strength, nor represents service conditions.

Other testing methods for such tubular products have been proposed, but none has been found to be suitable since all have deficiencies and disadvantages. One such testing method utilizes a belt wrapped around the tubular product and then pulled in tension to load the tube in radial compression. This belt testing method has serious deficiencies and disadvantages which include the fact that the load on the tube varies with the angle at which the belt is pulled. Another of these test methods involves direct loading of the tube by hydraulic fluid. Beyond the problems of direct contact of the hydraulic fluid with the tubular product being tested, difficulties in obtaining a reliable hydraulic seal and the general uncleanliness and operator inconvenience caused by an open hydraulic fluid system, direct hydraulic loading of tubular products initiates buckling rather than a compressive material failure.

Still another of these previously proposed testing methods utilized the radial loading in compression of tubular products by small balls surrounding the tubular product. The balls were loaded longitudinally by an axial testing machine through a mechanical plunger. However, this ball testing method did not provide uniform loading along the length of the curved surface of the tube. The results of this testing method were therefore unsuitable either for quality control or for research.

It is therefore an object of the present invention to provide an apparatus and method for testing the compressive strength of tubular products which overcomes the deficiencies and disadvantages of currently used and previously proposed testing methods and apparatuses.

SUMARY OF HTE INVNETION

The foregoing object of the invention is accomplished by an apparatus and method which are: (a) sufficiently reliable for both laboratory use and quality control testing in a production environment; (b) sufficiently simple and affordable to be located in the production area of a typical factory making tubular products; and (c) operable by persons having only those skills normally possessed by quality assurance personnel typically involved in the manufacture of tubular products. Additionally, the apparatus and method of the present invention provide: (a) uniform radial, compressive loading over the entire outside curved surface of the tube (both along the length and around the circumference) thereof; (b) loading in compression of the tube in such a manner that failure thereof is material in nature (compressive strength) rather than structural in nature (e.g. buckling); (c) for immediate detection and signaling of the onset of tube failure; and (d) for continuous monitoring of the magnitude of the pressure being applied to the outside curved surface of the tube.

The apparatus of the present invention includes a housing having an enclosed cylindrical cavity therein, tubular bladder means in the cavity defining a pressure chamber larger than the tube to be tested and a fluid receiving space between the bladder means and the inside wall of the housing, sufficient small balls to fill the pressure chamber around the tube being tested, and means for pumping hydraulic fluid into the fluid receiving space between the bladder means and the housing. The purpose of this fluid is to uniformly pressurize the balls and thereby apply uniform pressure over the entire external curved surface of the tube being tested. Pressure monitoring means is provided for continuously monitoring the pressure being applied and for immediately detecting the onset of failure of the tube.

BRIEF DESCRIPTION OF THE DRAWINGS

FIG. 1 is a perspective view of the apparatus of the present invention;

FIG. 2 is an exploded perspective view of the apparatus shown in FIG. 1;

FIG. 3 is a view similar to FIG. 1 with the top end cap removed to illustrate a tubular product in position to be tested;

DESCRIPTION OF THE PREFERED EMBODIMENT

Figure 4:
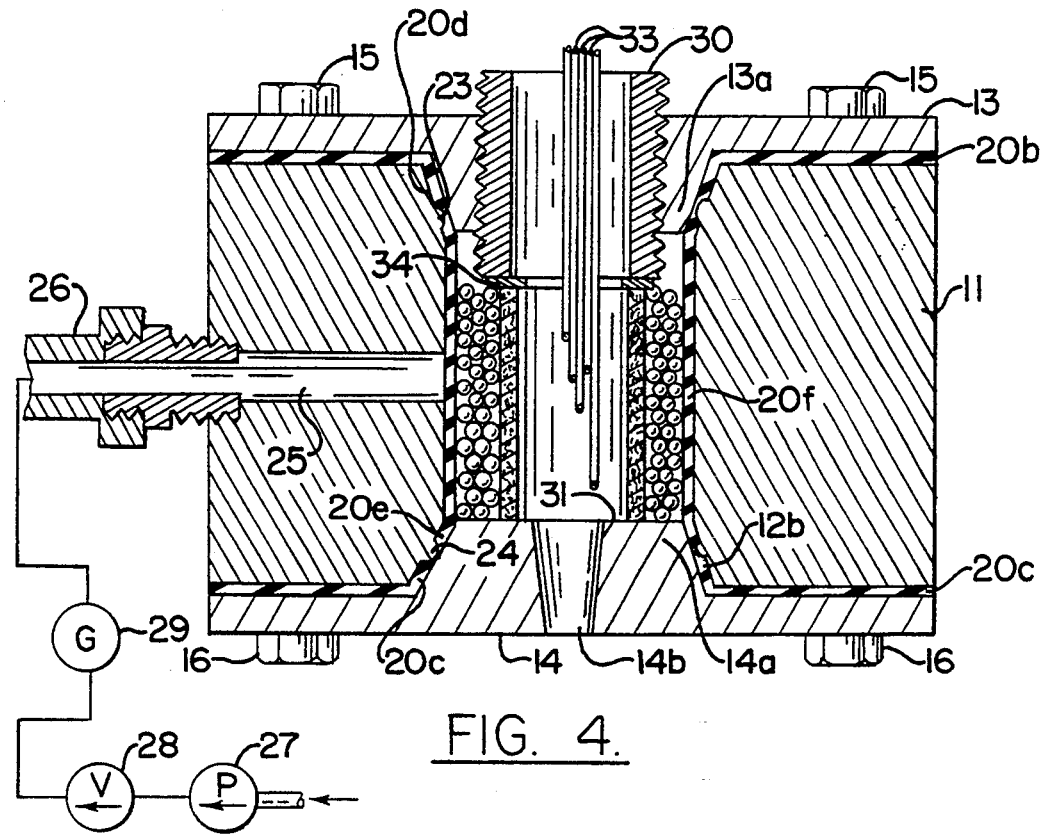
FIG. 4 is a sectional view taken substantially along line 4—4 in FIG. 1.

Referring more specifically to the drawings, there is illustrated therein an apparatus generally indicated at 10 incorporating the features of the present invention. Apparatus 10 comprises a housing 11 having a cylindrical cavity 12 therein. Cavity 12 preferably has the upper and lower end portions 12a and 12b thereof beveled outwardly.

A top end cap 13 is mounted on the top of housing 11 and has a frusto-conical portion 13a projecting into and closing the upper end of cavity 12. The bevel of the upper end 12a and the slope of conical portion 13a are preferably substantially the same for a close fit.

A bottom end cap 14 is mounted on the lower end of housing 11 and has a frusto-conical portion 14a projecting into and closing the lower end of cavity 12. The bevel of the lower end 12b and the slope of the conical portion 14a are preferably substantially the same for a close fit. Bevel angles of 14 degrees, measured from the longitudinal axis of the apparatus, were found to be suitable.

Preferably, top and bottom end caps 13, 14 are attached individually to housing 11 by bolts 15, 16 which penetrate holes 13c, 14c in the respective end caps and thread into blind, tapped holes 11a, 11b in housing 11. Obviously, end caps 13, 14 could alternatively be bolted collectively to housing 11 using full-length bolts which penetrate through holes extending the full length of housing 11. Suitable nuts could then be threaded on said full-length bolts to tighten end caps 13, 14 against housing 11. However, if full-length bolts were used, loosening one of the end caps would likely also loosen the other end cap and could thereby damage the hydraulic seal of the bladder means 20 at both ends thereof. When assembling the fixture prior to testing, it is also easier to seal the bladder means 20 correctly if each end cap 13,14 is bolted individually to the housing 11.

Bladder means 21 is positioned in cavity 12 of housing 11 and includes a cylindrical, tubular portion 20a and top and bottom flanges 20b and 20c to define a pressure chamber 21 therein. Top and bottom flanges 20b and 20c are positioned against the top and bottom ends of housing 11, respectively. The top and bottom end sections 20d, 20e of portion 20a of bladder means 20 are located respectively between the top and bottom beveled portions 12a, 12b of cavity 12 and the beveled surfaces of frusto-conical portions 13a, 14a of top and bottom end caps 13, 14. When top and bottom end caps 13, 14 are atached tightly to housing 11 by bolts 15, 16, through holes 20b', 20c' in the flanges 20b, 20c of the bladder means 20, the top and bottom end sections 20d, 20e of the tubular portion 20a of bladder means 20 become outwardly stretched and clamped between the beveled faces of frusto-conical portions 13a, 14a of end caps 13, 14 and beveled portions 12a, 12b of housing cavity 12. Bolting end caps 13, 14 to housing 11 leaves a central, straight, tubular portion 20f of portion 20a of bladder means 20 and defines a fluid receiving space 22 between bladder means 20 and the wall of cavity 12 of housing 11.

Bladder means 20 is preferably formed of rubber and may be fiber-reinforced or non-reinforced. Also, bladder means 20 may be flanged as described above or unflanged. Whether or not bladder means 20 has flanges, upper and lower sections 20d, 20e of portion 20a of bladder means 20 are pinched between the beveled surfaces of conical frustum portions 13a, 14a of end caps 13, 14 and beveled end portions 12a, 12b of cavity 12.

Preferably, bladder means 20 is made of an oil-resistant rubber having a durometer of 55 to 65. One rubber that has been used successfully is Duro-Bruna N (Hycar) having the following formulation, expressed as a percentage by weight:

| Material | Amount |
| --- | --- |
| Hycar QR-25 (1032) | 53.48 |
| Zinc Oxide | 2.67 |

-continued

| Material | Amount |
| --- | --- |
| Sulfur | 1.07 |
| Altax | 0.80 |
| Agerite Alba | 1.07 |
| P-33 Carbon Black | 26.74 |
| Stearic Acid | 0.80 |
| Dibutyl Phthalate | 13.37 |
| Total | 100.00 |

To ensure proper sealing of the sections 20d, 20e of portion 20a of bladder means 20, housing 11 in the beveled portions 12a and 12b of cavity 12 preferably have annular ribs 23, 24 projecting therefrom toward frusto-conical portions 13a, 14a of end caps 13, 14. Ribs 23, 24, respectively, engage and apply sealing pressure to sections 20d, 20e of portion 20a of bladder means 20 to ensure no leakage of fluid from fluid receiving space 22. Obviously, ribs 23, 24 could be provided on frusto-conical portions 13a, 14a instead of on the beveled end portions 12a, 12b of cavity 12.

Figure 5:
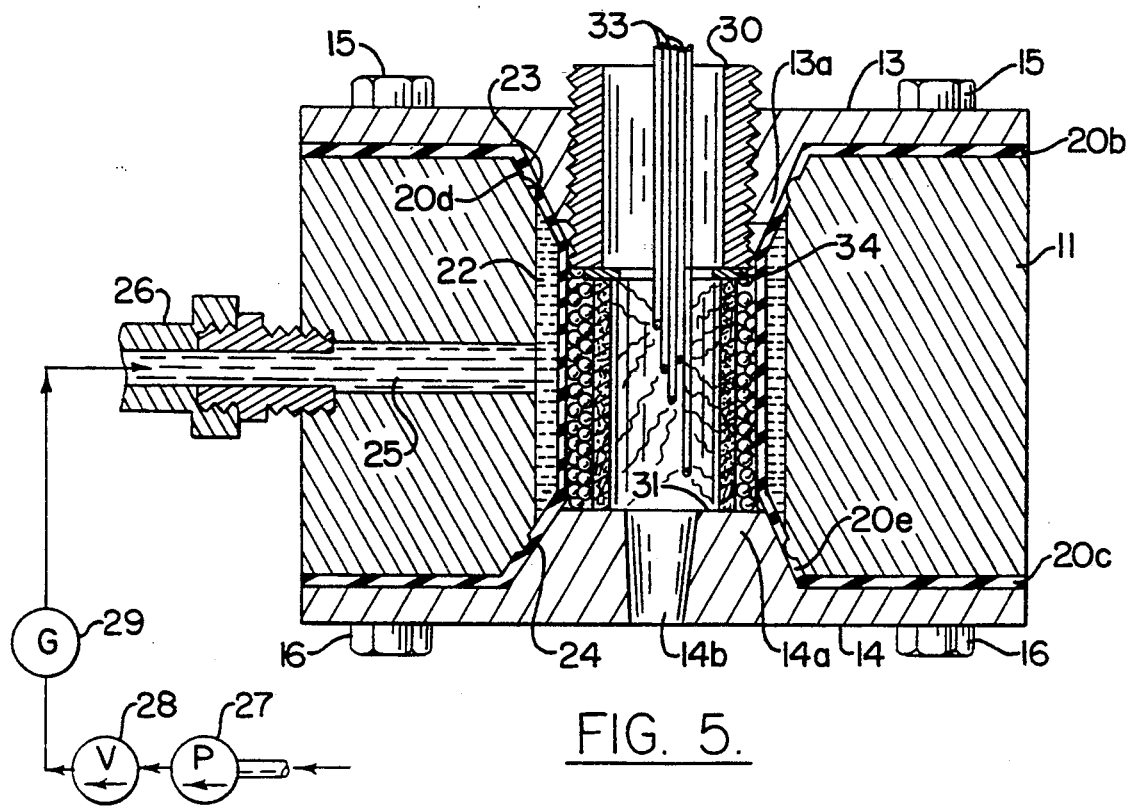
FIG. 5 is a sectional view similar to FIG. 4 illustrating hydraulic fluid being pumped into the space between the bladder means and the housing to apply pressure to a tube being tested.
Figure 6:
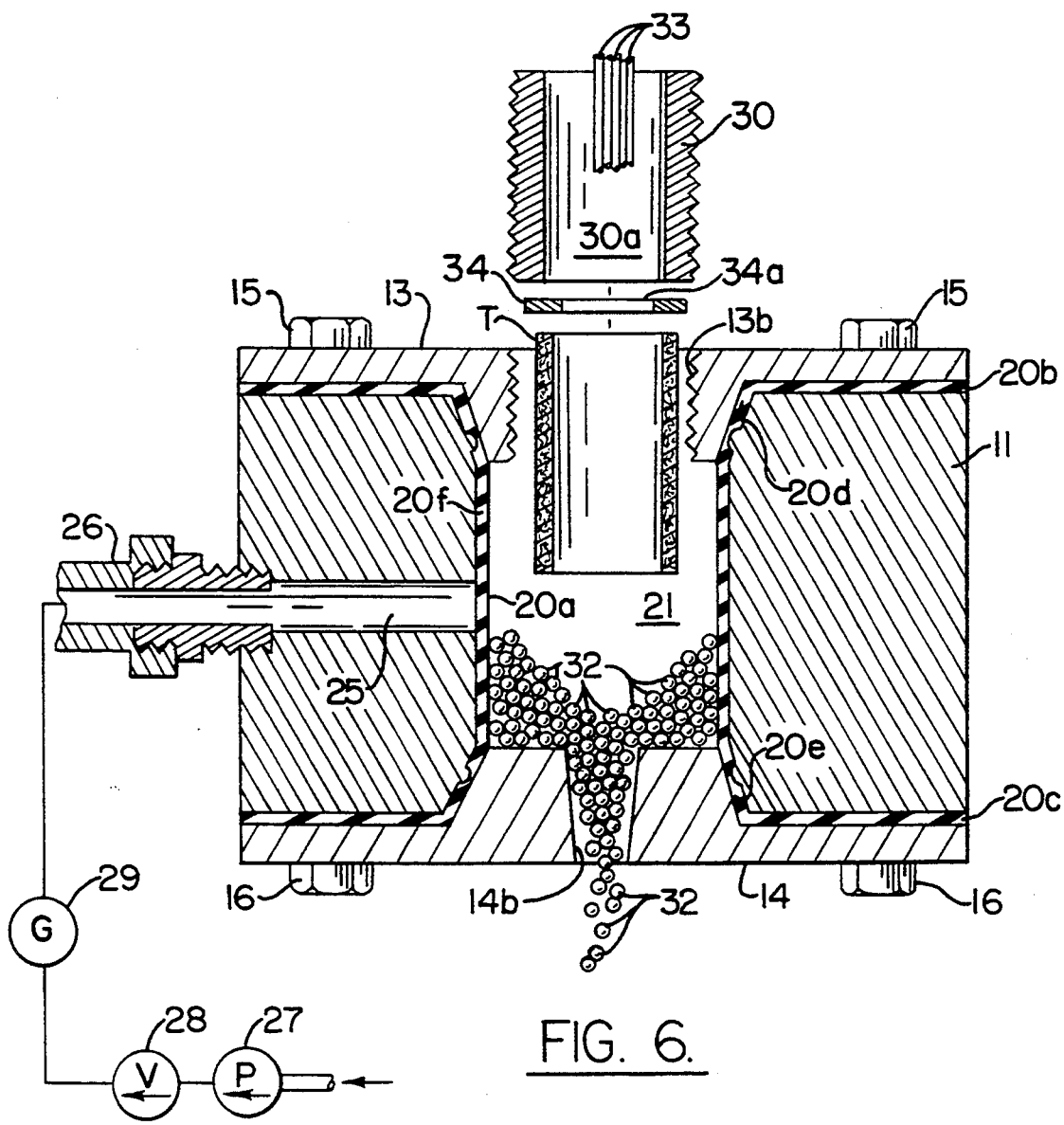
FIG. 6 is a view similar to FIGS. 4 and 5 illustrating the removal of a tube after testing and the removal of the small balls from the pressure chamber.

Housing 11 contains a fluid inlet port 25 which is connected to fluid receiving space 22 and has one end of a hydraulic fluid supply hose 26 attached thereto. The other end of hose 26 is attached to hydraulic pump means 27 for pumping hydraulic fluid into the fluid receiving space 22 through suitable valve means 28 (FIGS. 4 through 6). Preferably, a pressure gage 29 is attached to supply hose 26 to monitor and display the pressure in the supply hose 26 and thus the pressure in fluid receiving space 22.

Top end cap 13 has an internally threaded, centrally located fill opening 13b therethrough (FIG. 6). Fill opening 13b is normally closed by an externally threaded plug 30. The lower end of plug 30 is adapted to press against and hold in position a tube T being tested.

The upper surface 31 of frusto-conical portion 14a functions as a tube receiving and supporting platform. The tube T being tested rests on and is held in pressure chamber 21 during testing by platform 31 and the lower end of plug 30. Surface 31 of the lower end cap 14 preferably has a tapered port 14b centrally located therein for reasons to be described hereinafter.

A plurality of small balls 32 is placed in pressure chamber 21 in surrounding relation to the tube T being tested. Balls 32 are sufficient in number to fill substantially the space between the tube and the inside surface of the tubular portion 20f of bladder means 20. While any suitable size of the small balls 32 may be used, balls of one-sixteenth inch (1/16") diameter have been used successfully.

Balls 32 are added to pressure chamber 21 through fill opening 13b in top end cap 13 when plug 30 is removed. The balls 32 are removed through the tapered opening 14b centrally located in bottom end cap 14 when a test is completed.

Plug 30 may have an access opening 30a therein to provide access to the interior of the tube T being tested. Access opening 30a provides for suitable monitoring means or instrumentation, such as strain gages, to be attached in known manner to the tube T being tested with lead wires passing through access opening 30a to external equipment (not shown). Strain-gaged paper and aluminum tubes have been tested successfully in accordance with this invention.

In the operation of apparatus 10 and in accordance with the method of the present invention, a test procedure is initiated by removing the plug 30 from top end cap 13 and inserting a tubular specimen T to be tested through fill opening 13b into pressure chamber 21 onto supporting platform 31. It is noted that the tubular specimen T is larger than the tapered opening 14b through bottom end cap 14 so that the opening 14b is closed by the tube T.

The tube T may be of any suitable type material, diameter, wall thicknesses, or shape. For example, both aluminum tubes and paper tubes of various different diameters and wall thicknesses have been successfully tested using the same assembly (same housing, end caps, etc.) in accordance with this invention.

Compliant ring 34 of thick paper, thin cardboard, Teflon or rubber is typically placed between the top of the specimen tube T and the bottom of plug 30. The purpose of compliant ring 34 is to permit the tube T to deform radially due to the external pressure and longitudinally because of the Poisson effect. Ring 34 has a central opening 34a therein to permit lead wires 33 to be passed therethrough.

The balls 32 are poured into pressure chamber 21 around the outside of the specimen tube T until the pressure chamber 21 is substantially filled to the top of the tube T. If desired, an appropriate funnel or other guide means (not shown) may be used to assist in pouring the balls 32 into pressure chamber 21.

If desired, and as is frequently the case, the specimen tube T can be equipped with instrumentation, such as strain gages. The lead wires 33 of such instruments are passed through opening 34a of compliant ring 34, fill opening 13b in top end cap 13, and access opening 30a in plug 30. Plug 30 is then threaded into fill opening 13b until the bottom end of plug 30 snugly engages compliant ring 34 and ring 34 snugly engages the top of the tube T. Strain-gaged aluminum and paper tubular products have been tested successfully in accordance with this invention.

Hydraulic pump means 27 is then activated to pump hydraulic fluid into fluid receiving space 22. The fluid pressure is typically increased until the tube T fails. Assembly 10 has been operated regularly up to at least 1300 psi in accordance with this invention. This pressure of 1300 psi is more than adequate for testing most tubular products, but appreciably higher pressures may be employed within the scope of this invention. Bladder means 20 applies pressure uniformly to small balls 32 which, in turn, apply pressure uniformly over the entire external curved surface of the specimen tube T. Experimental results of strain-gaged aluminum tubes and strain-gaged paper tubes obtained during the development of this invention substantiate that the pressure applied to the external curved surface of the specimen tube T is substantially equal to the pressure of the hydraulic fluid in fluid receiving space 22.

The onset of failure of the specimen tube T is readily detectable by viewing pressure gage 29 which will indicate an instantaneous pressure drop at the onset of such failure. There is essentially no hysteresis upon loading and unloading. In addition, the response is reproducible and accuracy is sufficient for research as well as for quality control. Finally, compressive material strength is measured since tube T failures are material (not buckling) in nature.

In the drawings and specifications, there has been set forth a preferred embodiment of the invention, and, although specific terms are employed, they are used in a generic and descriptive sense only and not for purposes of limitation.

That which is claimed is:

1. Apparatus for experimentally determining the compressive material strength of tubular products comprising
   means defining a cylindrical cavity for receiving and supporting a tubular product during testing,
   tubular bladder means mounted in said cylindrical cavity and defining an internal pressure chamber larger than the tubular product to be tested and an external-fluid receiving space between said bladder means and said cavity defining means,
   a plurality of small balls substantially filling the internal space within said pressure chamber between said bladder means and the tubular product to be tested, and
   means for supplying fluid under pressure to said fluid receiving space between said bladder means and said cavity defining means so that said bladder means applies pressure to said small balls which in turn apply uniform pressure over the entire external curved surface of the tubular product being tested.

2. Apparatus according to claim 1 wherein said fluid supplying means is capable of supplying fluid under a pressure of up to at least 1300 psi so that a uniform radial pressure over the entire curved surface of the tubular specimen being tested is applied of up to at least 1300 psi.

3. Apparatus according to claim 1 including means for detecting and signaling tubular product failure.

4. Apparatus according to claim 1 including means for monitoring the pressure applied to the tubular product.

5. Apparatus according to claim 1 wherein said cavity defining means comprises a housing having a cylindrical cavity therein and top and bottom enid caps removably attached to said housing to close opposite ends of said cavity.

6. Apparatus according to claim 5 wherein said bladder means comprises a hollow cylindrical tubular portion and outwardly extending clamped top and bottom sections at opposite ends of said tubular portion, the internal diameter of said tubular portion being larger than the external diameter of the tube to be tested and the external diameter of said tubular portion being less than the diameter of said cavity in said housing.

7. Apparatus according to claim 6 wherein said top and bottom end sections of the tubular portion of the bladder means are sealingly engaged by the said top and bottom end caps to define a fluid-tight space between said housing and said bladder means.

8. Apparatus according to claim 1 wherein said fluid supplying means comprises hydraulic pump means for pumping hydraulic fluid into said fluid receiving space between said cavity defining means and said bladder means.

9. Apparatus for experimentally determining the compressive material strength of tubular products comprising
   housign means defniign acylindrical caviyt for receiving and suporting a tubluar product during testing,
   top and bottom end caps removably attached to said housing means for closing the top and bottom ends of said cylindrical cavity, bladder means mounted in said cylindrical cavity and comprising a tubular portion having an internal diameter greater than the external diameter of the tubular products to be tested to define an internal pressure chamber larger than the tubular product to be tested and having an external diameter less than the diameter of said cylindrical cavity to define an external fluid receiving space between said bladder means and said housing means, said bladder means having top and bottom end sections of the tubular portion of said bladder means sealingly engaged by said top and bottom end caps, a plurality of small balls substantially filling said internal pressure chamber between said bladder means and the tubular product to be tested, means for supplying the fluid under pressure to said fluid receiving space between said bladder means and said housing means so that said bladder means uniformly applies pressure to said small balls which in turn apply uniform pressure over the entire external curved surface of the tubular product being tested, and means for monitoring and displaying the pressure applied to the tubular product.

10. Apparatus according to claim 9 wherein said pressure monitoring and displaying means comprises pressure detecting means for detecting the pressure applied to the surface of the tubular product being tested and for generating a pressure indicating signal, and receiving means for receiving the pressure indicating signal from said pressure detecting means and for displaying the magnitude of the pressure applied to the tubular product.

11. Apparatus according to claim 9 wherein said fluid supplying means comprises hydraulic pump means connected to said housing means and communicating with said fluid receiving space for pumping hydraulic fluid under pressure into said space and forcing said tubular portion of said bladder means against said balls which in turn apply uniform pressure over the curved surface of the tubular product being tested.

12. Apparatus according to claim 9 wherein said top end cap includes a threaded, removable plug whose removal provides a fill opening through which a tubular specimen can be inserted into, or removed from said appartus without disrupting a hydraulic seal of said bladder means.

13. Apparatus according to claim 9 wherein said bottom end cap has a ball removing port therein.

14. A method of experimentally determining the compressive strength of tubular products comprising supporting a tubular product to be tested in a cylindrical pressure chamber defined by tubular bladder means, said pressure chamber having an internal space larger than the tubular product to be tested, substantially filling the internal space between said bladder means and the tubular product to be tested with small balls, and externally pressurizing said bladder means to apply pressure uniformly to said small balls which in turn apply uniform pressure over the entire curved surface of the tubular product being tested.

15. A method according to claim 14 wherein the bladder means is pressurized by hydraulic fluid to apply a pressure of up to at least 1300 psi to the tubular product being tested.

16. A method according to claim 14 including monitoring and displaying the pressure applied to the tubular product being tested.

17. A method according to claim 16 including detecting and signaling tubular product failure.

* * * * *

UNITED STATES PATENT AND TRADEMARK OFFICE
CERTIFICATE OF CORRECTION

PATENT NO. : 5,339,693
DATED : August 23, 1994
INVENTOR(S) : Rowlands et al

It is certified that error appears in the above-identified patent and that said Letters Patent is hereby corrected as shown below:

Column 1, line 10, "BACKGROND OF THE INVNETION" should be -- BACKGROUND OF THE INVENTION --.

Column 2, line 1, "SUMARY OF HTE INVNETION" should be -- SUMMARY OF THE INVENTION --.

Column 2, line 57, "PREFERED" should be -- PREFERRED --.

Column 3, line 27, "21" should be -- 20 --.

Column 3, line 38, "atached" should be -- attached --.

Column 4, line 65, after "wires" insert -- 33 --.

Column 6, line 13, "external-fluid" should be -- external fluid --.

Column 6, line 39, "enid" should be -- end --.

Column 6, line 63, "housign means defniign acylindrical caviyt" should be -- housing means defining a cylindrical cavity --.

Column 6, line 64, "suporting a tubluar" should be -- supporting a tubular --.

UNITED STATES PATENT AND TRADEMARK OFFICE
CERTIFICATE OF CORRECTION

PATENT NO. : 5,339,693
DATED : August 23, 1994
INVENTOR(S) : Rowlands et al

It is certified that error appears in the above-indentified patent and that said Letters Patent is hereby corrected as shown below:

Column 8, line 10, "appartus" should be -- apparatus --.

Signed and Sealed this

Fifteenth Day of November, 1994

Attest:

BRUCE LEHMAN

*Attesting Officer*  *Commissioner of Patents and Trademarks*